United States Patent
Wolf

(10) Patent No.: US 7,485,105 B2
(45) Date of Patent: Feb. 3, 2009

(54) TRANSCUTANEOUS TELEMETRY OF CEREBROSPINAL FLUID SHUNT PROGRAMMABLE-VALVE PRESSURE USING NEAR-INFRARED (NIR) LIGHT

(76) Inventor: Erich W. Wolf, 721 Bayou Pines East, Lake Charles, LA (US) 70601

( * ) Notice: Subject to any disclaimer, the term of this patent is extended or adjusted under 35 U.S.C. 154(b) by 251 days.

(21) Appl. No.: 11/067,497

(22) Filed: Feb. 25, 2005

(65) Prior Publication Data

US 2005/0187509 A1   Aug. 25, 2005

Related U.S. Application Data

(60) Provisional application No. 60/547,691, filed on Feb. 25, 2004, provisional application No. 60/577,807, filed on Jun. 8, 2004, provisional application No. 60/582,337, filed on Jun. 23, 2004.

(51) Int. Cl.
  *A61M 5/00* (2006.01)
  *A61M 37/00* (2006.01)
  *F16K 31/02* (2006.01)

(52) U.S. Cl. ............... 604/9; 604/6.1; 251/129.11

(58) Field of Classification Search ........... 604/8–10, 604/4.01–6.16; 251/129.11–129.22; 607/30–33, 607/59–65; 600/561, 651
See application file for complete search history.

(56) References Cited

U.S. PATENT DOCUMENTS

| | | | |
|---|---|---|---|
| 3,672,252 A | | 6/1972 | Summers |
| 3,672,352 A | * | 6/1972 | Summers ............... 600/476 |
| 4,387,715 A | | 6/1983 | Hakim et al. |
| 4,595,390 A | | 6/1986 | Hakim et al. |
| 4,660,568 A | | 4/1987 | Cosman |
| 4,677,982 A | | 7/1987 | Llinas et al. |
| 4,772,257 A | * | 9/1988 | Hakim et al. ............... 604/9 |
| 4,787,886 A | | 11/1988 | Cosman |
| 4,807,662 A | * | 2/1989 | Verne ............... 137/554 |
| 4,885,002 A | | 12/1989 | Watanabe et al. |
| 5,704,352 A | | 1/1998 | Tremblay et al. |
| 5,741,246 A | | 4/1998 | Prescott |
| 5,852,413 A | * | 12/1998 | Bacchi et al. ............... 341/13 |
| 5,873,840 A | | 2/1999 | Neff |
| 5,928,182 A | | 7/1999 | Kraus et al. |
| 6,049,727 A | | 4/2000 | Crothall |
| 6,050,969 A | | 4/2000 | Kraus |
| 6,126,595 A | | 10/2000 | Amano et al. |
| 6,162,238 A | | 12/2000 | Kaplan et al. |

(Continued)

*Primary Examiner*—Leslie R Deak
*Assistant Examiner*—Phil Wiest
(74) *Attorney, Agent, or Firm*—Schultz & Associates, P.C.

(57) ABSTRACT

An improvement for a programmable valve system of the type which is implanted in a medical patient and used to divert cerebrospinal fluid (CSF) from an intraventricular space of the patient to a terminus such as the patient peritoneal cavity. Such system includes means for establishing a flow path for the CSF to the terminus, which flow path includes a normally closed valve and means for adjusting the opening pressure of the valve in order to regulate the quantity of CSF diverted. The improvement enables an operator to be apprised of the actual opening pressure setting of the valve. A sensor is implantable at the patient and responds to the actual opening pressure setting, by generating an NIR telemetry signal indicative of the actual setting. This signal is transcutaneously transmitted through the skin of the patient to an external point. The telemetry signal is processed to produce observer intelligible data indicating the opening pressure setting of the valve.

14 Claims, 5 Drawing Sheets

U.S. PATENT DOCUMENTS

| | | |
|---|---|---|
| 6,241,660 B1 | 6/2001 | Dolle |
| 6,243,608 B1 * | 6/2001 | Pauly et al. .................. 607/60 |
| 6,413,267 B1 * | 7/2002 | Dumoulin-White et al. ... 607/89 |
| 6,439,538 B1 | 8/2002 | Ito |
| 6,533,733 B1 * | 3/2003 | Ericson et al. .............. 600/561 |
| 2005/0010159 A1 | 1/2005 | Reich et al. |
| 2005/0038371 A1 | 2/2005 | Reich et al. |
| 2005/0085763 A1 | 4/2005 | Ginggen et al. |
| 2005/0148925 A1 | 7/2005 | Rottenberg et al. |

* cited by examiner

TRANSCUTANEOUS TELEMETRY OF CEREBROSPINAL FLUID SHUNT PROGRAMMABLE-VALVE PRESSURE USING NEAR-INFRARED (NIR) LIGHT

RELATED APPLICATIONS

This application claims priority from U.S. Provisional Applications 60/547,691 filed Feb. 25, 2004; 60/577,807 filed Jun. 8, 2004; and 60/582,337 filed Jun. 23, 2004.

FIELD OF INVENTION

This invention relates generally to transcutaneous telemetry with an implantable biomedical device, and more specifically relates to a system which allows transcutaneous telemetry of a programmed valve opening pressure via near-infrared (NIR) light.

BACKGROUND OF THE INVENTION

Fluidic shunts are commonly employed for the diversion of cerebrospinal fluid from the cranial intraventricular space to a terminus such as the peritoneal cavity in the treatment of hydrocephalus. The quantity of cerebrospinal fluid (CSF) diverted by the shunt may be altered by adjusting the opening pressure of a normally closed integral valve. Several valve designs (e.g. Codman-Hakim® valve, Medtronic Strata® valve) allow transcutaneous adjustment, or programmability, of the opening pressure via a transcutaneously applied magnetic field.

The programmed valve pressure is dependent upon the position of the external programmer relative to the implanted valve. Because the valve is implanted beneath the skin, the exact orientation of the valve is not always apparent. Malpositioning of the programmer can introduce errors into the programming process and result in erroneous pressures being programmed. Therefore, it is desirable to be able to confirm the actual programmed pressure after reprogramming or as clinical conditions warrant. By "actual" programmed pressure is meant the de facto pressure which has been set for opening of the valve as opposed to the pressure which may be assumed to have been set as a result of the operator's manual adjustment.

While the Medtronic Strata® valve provides a transcutaneous means of magnetically indicating the valve pressure setting, the Codman-Hakim valve requires the use of an x-ray to determine the valve setting. The use of x-ray to determine valve pressure is undesirable as it is costly, time-consuming, and exposes the patient to ionizing radiation.

SUMMARY OF INVENTION

The invention disclosed herein provides an improvement pertinent to existing programmable valve systems which allows transcutaneous telemetry of programmed valve opening pressure via near-infrared (NIR) light. NIR light easily penetrates body tissues such as the scalp, and the light beam may be modulated to encode data for transcutaneous transmission. The actual valve pressure setting is determined by an attached cam. An optical disc coaxially mounted with the cam optically encodes the valve position and these data are transmitted extracorporally via NIR light.

Light in the near-infrared spectrum is easily transmitted through the skin and is detected by an external sensor head and associated electronics. Indefinite longevity and small size is attained in the implant by not incorporating a power source within the module. Instead, power is derived inductively through rectification of a transcutaneously-applied high-frequency alternating electromagnetic field which is generated by a power source within the external coupling module, in concept much like a conventional electrical transformer. The extracorporeal components of the system calculate the actual valve opening pressure setting.

The present invention overcomes the aforementioned disadvantages of existing technologies by providing a means for telemetric conveyance of physiological data via transcutaneous projection of a near infrared light beam. The use of this technique for telemetry of intracranial pressure and other applications is set forth in my co-pending U.S. patent application Ser. No. 11/065,428 filed Feb. 24, 2005. The entire disclosure of that application is hereby incorporated herein by reference.

The NIR spectrum is defined as 750-2500 nm. Choice of the preferred NIR wavelength for transcutaneous telemetry pursuant to the present invention is dependent upon the absorption coefficients of the intervening tissues. The absorption by melanosomes dominates over the visible and near-infrared spectra to about 1100 nm, above which free water begins to dominate. Absorption by the dermis decreased monotonically over the 700-1000 nm range. Whole blood has a minimum absorption at about 700 nm but remains low over the 700-1000 nm range. The nadir in the composite absorption spectrum therefore lies in the 800-1000 nm range.

The actual wavelength utilized is therefore dictated by the optimal spectral range (as above) and the availability of suitable semiconductor emitters. Several suitable wavelengths may include, but are not limited to: 760 nm, 765 nm, 780 nm, 785 nm, 790 nm, 800 nm, 805 nm, 808 nm, 810 nm, 820 nm, 830 nm, 840 nm, 850 nm, 870 nm, 880 nm, 900 nm, 904 nm, 905 nm, 915 nm, 920 nm, 940 nm, 950 nm, 970 nm, and 980 nm. Wavelengths outside this range may be used but will be subject to greater attenuation by the intervening tissues.

BRIEF DESCRIPTION OF DRAWINGS

The invention is diagrammatically illustrated, by way of Example, in the drawings appended hereto, in which.

DESCRIPTION OF THE PREFERRED EMBODIMENT

Figure 1:
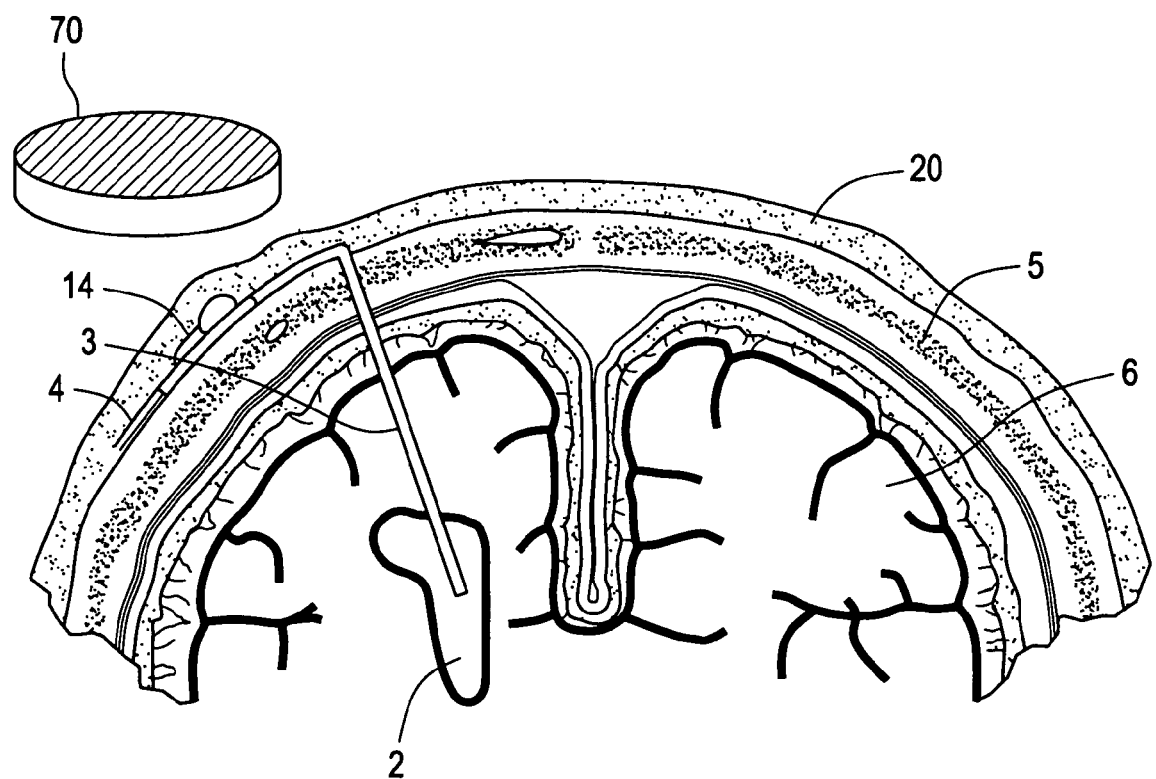
FIG. 1 is a simplified longitudinal cross sectional diagram illustrating how the sensor may be implanted in a typical use with a patient.

The system of the present invention as shown in the simplified cross-sectional view of FIG. 1 includes an extracorporeal sensor head 70 which provides an interface to a human operator and which telemeters with an implanted component 14. The latter is integrated into the shunt-valve housing, detects the actual valve setting, and telemeters these data to the extracorporeal sensor head 70. The implanted component 14 may derive its power via inductive coupling from the extracorporeal sensor head 70.

Figure 2:
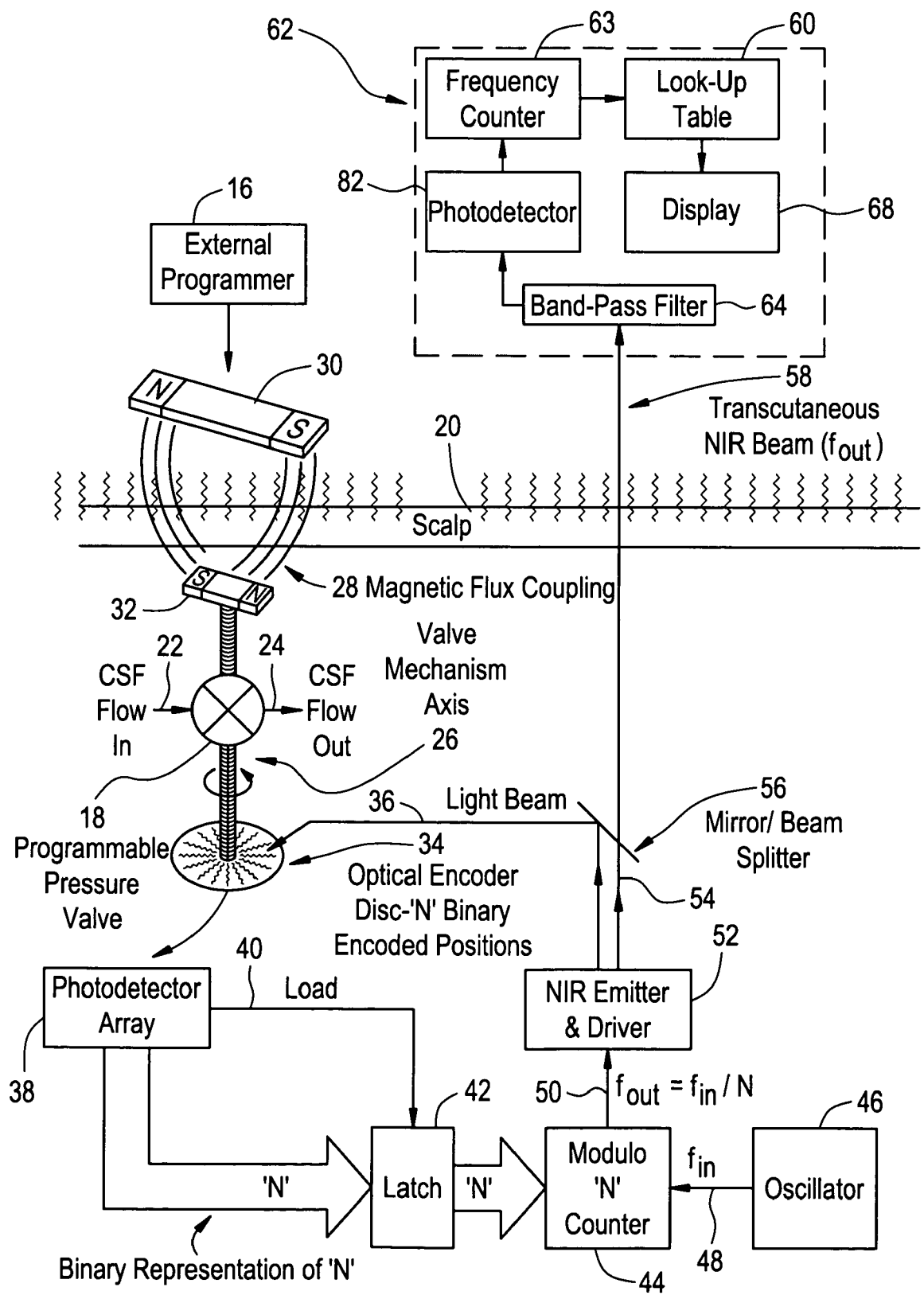
FIG. 2 is a schematic diagram, partially in block form, illustrating an overall system in accordance with the invention.

In a typical in vivo implementation a hollow ventricular catheter 3 is placed surgically into a cerebrospinal fluid (CSF) filled ventricle 2 of the brain 6 of the patient. The CSF is communicated via the ventricular catheter 3 to the implanted component 14 where its flow is controlled by controllable pressure valve 18 (FIG. 2). The normally closed valve opening pressure setting is controlled by an attached cam which is mounted on a rotatable axis. An optical disc on that axis acts with other elements to encode the valve position, data for which is transmitted extracorporally through skin 20 via NIR light to sensor head 70. Depending on valve position, the CSF may exit the implanted sensor 14 and passes, via distal catheter 4, ultimately to the peritoneal cavity of the abdomen (not shown) or other appropriate point. The implanted sensor 14 is installed superficial to, or embedded within the skull 5.

FIG. 2 depicts a schematic block diagram of a preferred embodiment of the ICP Valve transducer system. External programmer 16 is an extracorporeal device which is used to set the opening pressure of a programmable pressure valve 18 which is implanted beneath the skin (scalp) 20 of the patient. The opening pressure of normally closed valve 18 dictates the maximum pressure gradient between the cerebrospinal fluid compartment which is connected to inlet 22 to valve 18, and the outflow for which is via outlet 24. The valve 18 pressure setting is dependent upon the position of a cam which rotates around the valve's mechanical axis 26.

The external programmer 16 is able to modify the rotational position of the valve 18 mechanical axis 26 via magnetic flux 28 coupling between an external magnet 30 and a magnet 32 fixedly attached to the mechanical axis 26 of the valve mechanism. The technology referenced by items 16 through 32 is described in the prior art.

In prior art valves exemplified by valve 18, detents within the valve mechanism define specific rotational angles in which the valve mechanism axis 26 may remain in a static position. In the preferred embodiment of the current invention, an optical encoder disc 34 secured to axis 26 is an optically opaque disc with radially oriented perforations (or optically transparent windows) which encode binary numerals. Each specific static rotational angle which may be assumed by the valve mechanism axis 26 has a corresponding unique encoded binary numeral, n. An NIR light beam 36 transilluminates the optical encoder disc 34 such that the binary encoded numeral, n, may be detected by photodetector array 38. In the preferred embodiment, these encoded numerals are arranged sequentially around the disc 34 ranging from 1 to 'N' where N is the total number of discrete static positions of the valve mechanism axis 26. A valid encoded numeral, n, is detected by the photodetector array 38 only during transillumination of the encoder disc 34 by NIR light beam 36. A "data valid" command is generated by logical OR of each of the bits of the binary encoded numeral, n, or by using a single separate photodetector with an additional optical window at each discrete static position of the valve mechanism axis 26. The "data valid" signal provides a 'load' command 40 to a latch 42 which stores the encoded binary numeral, n.

The encoded binary numeral, n, is used as the divisor for a modulo-n counter 44. A crystal oscillator 46 provides a stable reference frequency 48, $f_{in}$, which is divided by the divisor ratio, n. Therefore, the output frequency 50, $f_{out}$, is uniquely dependent upon the valve mechanism axis 26 position, and hence the pressure to valve 18. The near infrared emitter 52 is driven at the output frequency 50. The infrared beam 54 is passed through a beam-splitter mirror 56 such that a portion of the infrared light beam 36 is used to transilluminate the optical encoder disc 34. The remainder of beam 54 travels through the skin 20 to become the transcutaneous NIR beam 58. The transcutaneous beam 58 is detected by a photodetector 82 within sensor head and processing electronics 62 after passing through a narrow bandpass filter 64. The narrow bandpass filter 64 excludes ambient light at wavelengths other than that expected from the NIR emitter 52. The frequency of the photodetector 82 output is measured at 63 and is used to index a look-up table 60 which correlates the modulation frequency 50 with the actual valve pressure setting which is then displayed at 68.

Figure 3:
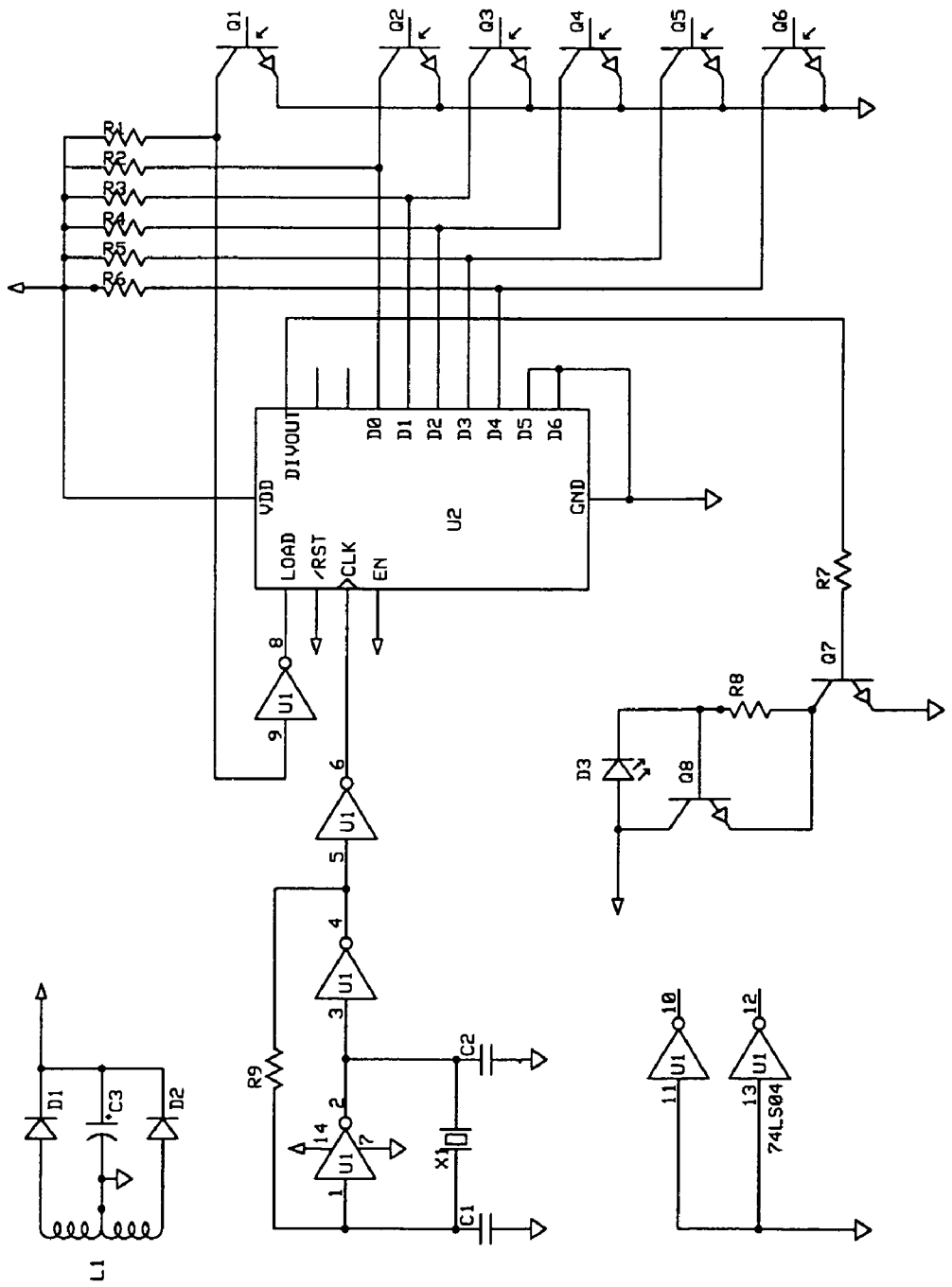
FIG. 3 is an electrical schematic diagram of the valve pressure transducer and associated components.

FIG. 3 illustrates representative electronic circuitry for the implant. A crystal oscillator composed of crystal X1, inverters U1a-c, capacitors C1, C2 and feedback resistor R9, provides a reference frequency to programmable divider U2. The reference frequency is divided by modulo-N and the output used to gate the VCSEL, D3, via transistor Q7. Transistor Q8 and resistor R8 act to regulate the maximum current through D3.

Light from the VCSEL is detected by an array of photodetectors Q1-Q6. During VCSEL illumination, the disc 34 (FIG. 2) allows selective illumination of phototransistors Q2-Q6, thus providing a binary representation of the modulo-N. The light path from the VCSEL to Q1 is never obstructed, despite the position of disc 34 so that Q1 conducts each time the VCSEL illuminates. The output of Q1 is fed to inverter U1d which, in turn, asserts a positive-going 'load' signal to U2 as the VCSEL illuminates. Upon assertion of the 'load' signal, the divider modulo-N data is latched on U2 inputs D0-D4. A small capacitance, on the order of several picofarads, may be placed on the base of transistor Q1 to allow Q2-Q6 to stabilize prior to asserting the 'load' signal. A period of $2^N$ clock pulses may be necessary for the output frequency to stabilize.

Figure 4:
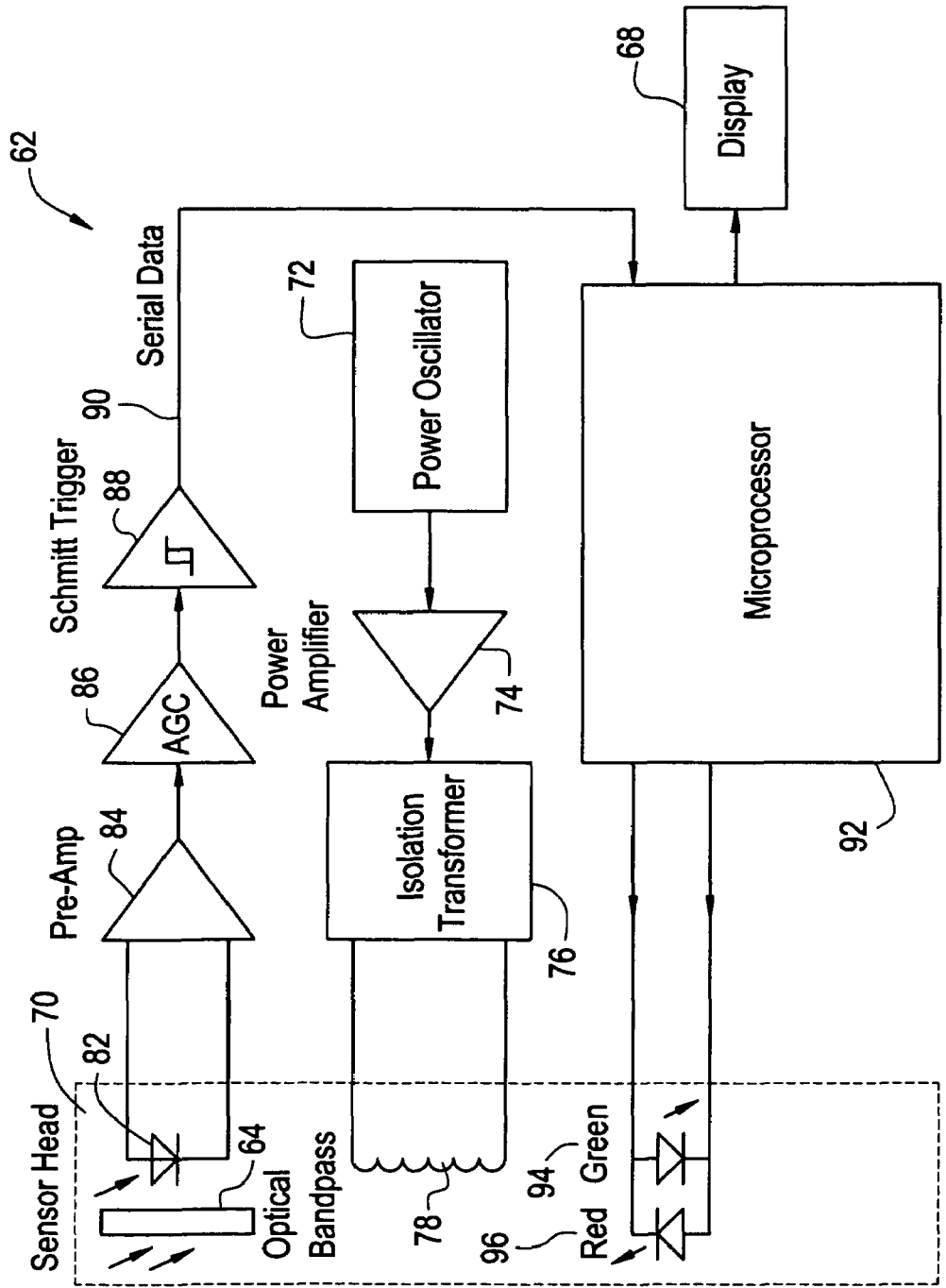
FIG. 4 is a schematic block diagram of the valve position sensor components which are external to the patient.
Figure 5:
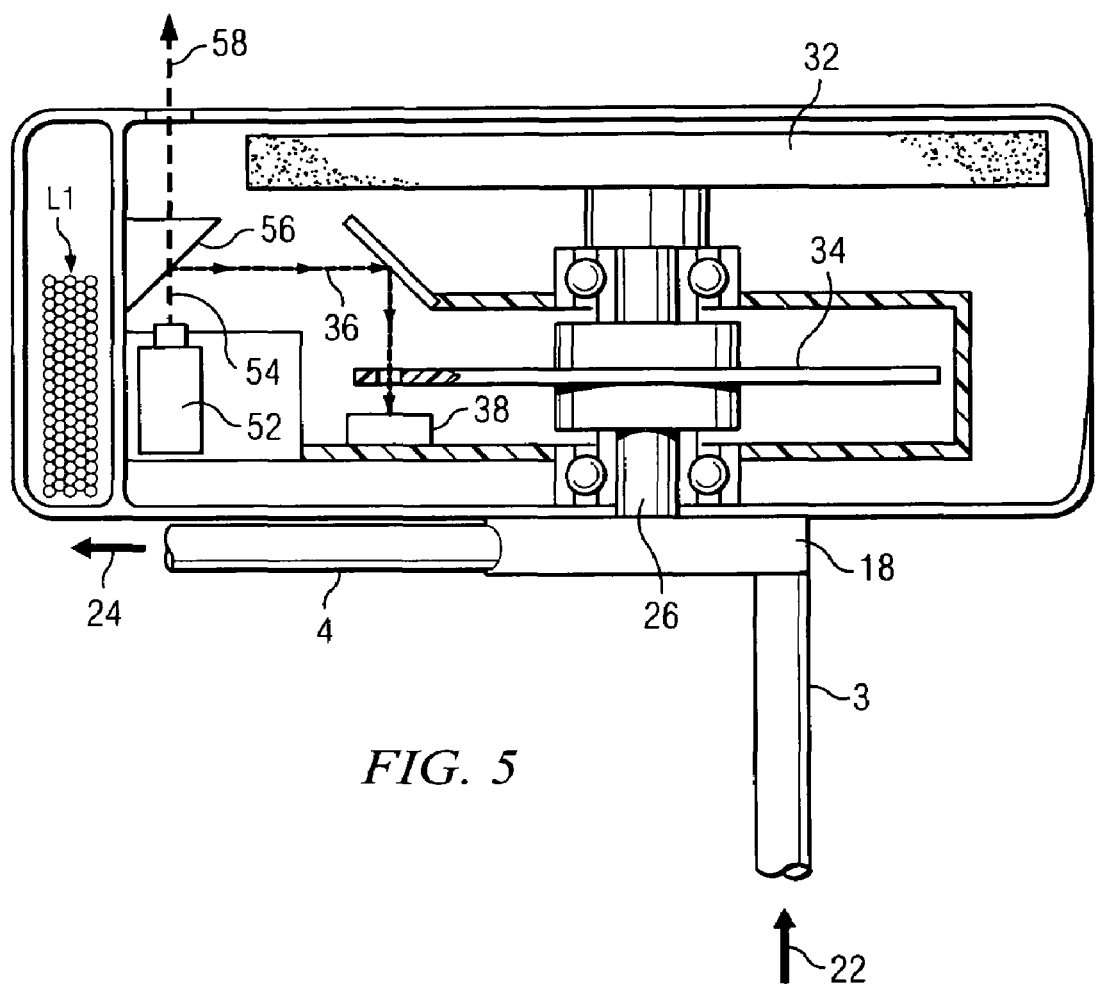
"FIG. 5 is a non-schematic diagram of the relationship and positioning of the optical encoder and magnetic flux coupling of the invention."

FIG. 4 depicts a block diagram of the external circuitry which: 1) provides power to the implant; 2) detects the NIR emission from the implant; and, 3) converts the frequency data from the implant to a graphical representation of valve position.

Sensor head 70 is placed over the implant to deliver power and detect the optical output of the implant. A power oscillator 72 delivers a sinusoidal oscillating current with a nominal frequency of 200 kHz to a power amplifier 74 which buffers the current to an isolation transformer 76. The isolation transformer 76 provides adequate galvanic isolation for a patient-connected device. The output from the isolation transformer is fed to the sensor head coil 78 which acts as the primary winding of a transformer to electromagnetically couple energy to the implant's secondary coil L1 (FIG. 3).

An optical bandpass filter 64 with center frequency equal to the emission frequency of the VCSEL, excludes ambient light from the photodetector 82. Light from the implant VCSEL is transmitted through bandpass filter 64 and converted to an electrical current by photodetector 82. This current is roughly a square wave with the same fundamental frequency as the VCSEL pulses. This signal is amplified by pre-amp 84 and automatic gain amplifier 86, then converted to a digital signal by Schmitt trigger 88. A serial data stream 90, consisting of square-wave pulses, is fed to microprocessor 92 which measures the frequency of the aforementioned pulses. The frequency data is then used to index a look-up table 60 (FIG. 2) through software programming; the result of which is a numerical indication of the valve pressure setting. The result is displayed for the user upon a digital or other graphical display 68.

A bi-colored Light Emitting Diode, or LED, is also included in the sensor head 70 to aid positioning of the sensor head over the implant. In the default state, the red LED 96 is illuminated to indicate that the sensor head is not over the implant. When the sensor head is properly aligned over the implant, the implant begins to receive power through the inductive coupling between coil 78 of the sensor head and L1 of the implant. Once power is applied to the implant, the VCSEL begins to illuminate in synchrony with the programmable divider (U2) output. When the External device begins to detect the VCSEL, e.g. oscillations present on the 'serial data' output of Schmitt Trigger 88, the microprocessor 92 turns off the red LED 96 and illuminates the green LED 94.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

The invention claimed is:

1. A system for regulating an internal programmable valve implanted in a medical patient comprising:
    a subcutaneous case;
    a valve in the case with access to an internal fluid;
    a subcutaneous magnet connected to the valve;
    a transcutaneous magnet;
    a magnetic flux coupling between the subcutaneous magnet and the transcutaneous magnet;
    an encoder disk within the case connected to the valve;
    a near infrared optical source producing a near infrared source signal;
    the near infrared source signal incident on the encoder disk;
    an optical receiver in communication with the near infrared source signal and generating an angular position signal related to the angular position of the encoder disk;
    a conversion circuit transforming the angular position signal into an encoded near infrared optical signal;
    the conversion circuit comprising a reference signal generated by a frequency generator, and a frequency divider in communication with the reference signal and the angular position signal;
    the near infrared optical source connected to the frequency divider and producing a transmitted near infrared optical signal;
    the near infrared optical source further comprising a beam splitter in the path of the transmitted near infrared optical signal, the beam splitter being adapted to partition the transmitted near infrared optical signal into the near infrared optical source signal and a transcutaneous near infrared data signal; and
    an inductive power coupling providing power to the near infrared optical source, the optical receiver and the conversion circuit.

2. The system of claim 1 wherein the encoder disk further comprises:
    an optically opaque disk having an encoder pattern;
    and wherein the near infrared optical source signal passes through the encoder pattern; and
    wherein the optical receiver includes a first reference array adjacent the optically opaque disk adapted to receive the transmitted near infrared source signal through the encoder pattern.

3. The system of claim 1 wherein the encoder pattern contains a binary code.

4. The system of claim 1 wherein the encoder pattern is a set of transparent sections in the encoder disk.

5. The system of claim 1 wherein the encoder pattern is a set of radially oriented perforations.

6. The system of claim 1 wherein the first reference array generates a numerical signal.

7. The system of claim 1 wherein a logical OR operation is used on the numerical signal to generate a data valid signal.

8. The system of claim 1 wherein the encoder disk further comprises:
    a reference pattern indicative of a valve position and wherein the near infrared optical source signal passes through the reference pattern; and
    a second reference array, adjacent the reference pattern, adapted to receive the near infrared optical source signal through the reference pattern and generate a signal indicative of an angular position of the encoder disk.

9. The system of claim 8 wherein the second reference array generates a data valid signal for storing an encoded number indicative of the angular position of the encoder disk.

10. The system of claim 9 wherein the data valid signal is a binary number.

11. The system of claim 8 wherein the number of angular positions is a range between 0 and 255.

12. The system of claim 1 wherein the internal fluid is cerebral spinal fluid.

13. The system of claim 1 wherein the encoded near infrared optical signal is in a wavelength range of about 800 nm to about 1000 nm.

14. The system of claim 1 wherein the encoded near infrared optical signal is in the range of about 760 nm to about 980 nm.

* * * * *